(12) United States Patent
Sparks

(10) Patent No.: US 6,942,169 B2
(45) Date of Patent: Sep. 13, 2005

(54) MICROMACHINED LYSING DEVICE AND METHOD FOR PERFORMING CELL LYSIS

(75) Inventor: Douglas Ray Sparks, Whitmore Lake, MI (US)

(73) Assignee: Integrated Sensing Systems, Ypsilanti, MI (US)

( * ) Notice: Subject to any disclaimer, the term of this patent is extended or adjusted under 35 U.S.C. 154(b) by 388 days.

(21) Appl. No.: 09/683,967

(22) Filed: Mar. 7, 2002

(65) Prior Publication Data

US 2002/0185557 A1 Dec. 12, 2002

Related U.S. Application Data

(60) Provisional application No. 60/295,846, filed on Jun. 6, 2001.

(51) Int. Cl.[7] .............................................. B02C 19/18
(52) U.S. Cl. .............................. 241/1; 241/2; 241/301; 435/259; 435/820
(58) Field of Search ................................ 241/1, 2, 301; 435/306.1, 820, 259; 73/861.352

(56) References Cited

U.S. PATENT DOCUMENTS 5,639,423 A * 6/1997 Northrup et al. ............. 422/50
6,100,084 A * 8/2000 Miles et al. ............. 435/306.1
6,431,476 B1 * 8/2002 Taylor et al. ................... 241/1
6,477,901 B1 * 11/2002 Tadigadapa et al. ... 73/861.352

OTHER PUBLICATIONS

Taylor, Michael, et al; *Lysing Bacterial Spores by Sonication Through a Flexible Interface in a Microfluidic System*, Analytical Chemistry, vol. 73, No. 3, Feb. 1, 2001, pp. 492–496.
Tzannis, Stelios T., *Tutorial on Cell Disruption*.
Smith, Tiffany J., *TechNotes 5(4), Cell Disruption: Getting the RNA Out*.

* cited by examiner

*Primary Examiner*—Mark Rosenbaum
(74) *Attorney, Agent, or Firm*—Gary M. Hartman; Domenica N. S. Hartman; Hartman & Hartman

(57) ABSTRACT

A method and device for performing lysing on a cell-containing fluid, in which the fluid flows through a vibrating micromachined tube to physically rupture the cell walls (mechanical lysis), and/or to mix, agitate or homogenize the fluid during chemical lysis, and/or to mix, agitate or homogenize the lysate for analysis or other processing after lysing. The tube includes a freestanding portion spaced apart from a surface of a substrate on which the tube is formed. The device further includes means for vibrating the freestanding portion of the tube at a level sufficient to rupture the walls of cells in a fluid flowing through the freestanding portion (for mechanical lysing) or to mix the fluid and a chemical lysing additive within the freestanding portion (for chemical lysing).

52 Claims, 2 Drawing Sheets

MICROMACHINED LYSING DEVICE AND METHOD FOR PERFORMING CELL LYSIS

CROSS REFERENCE TO RELATED APPLICATIONS

This application claims the benefit of U.S. Provisional Application No. 60/295,846, filed Jun. 6, 2001.

BACKGROUND OF INVENTION

1. Field of the Invention

The present invention generally relates to cell disruption (lysing) methods and equipment. More particularly, this invention relates to a lysing device and method that utilize a vibrating micromachined tube through which biological cells, spores or other cellular matter flows to produce or promote the cell lysing process.

2. Description of the Related Art

Cell disruption, or lysis, involves releasing the biological molecules within a cell by physically or chemically rupturing the cell wall. Lysis of biological cells and spores is used in a variety of biological research and development activities, including the analysis of DNA, the isolation of RNA, the extraction of hemoglobin from red blood cells, the separation of cellular parasites, the detection of pathogens, enzyme concentration, vaccine production, and cancer cell research. After lysing, filtration may be performed to remove small fragments of the cell walls if total cell disruption has occurred, immediately followed by analysis of the released biological molecules and cellular components (lysate) to avoid denaturation of the released materials. Various chemical and biological analysis techniques may be performed on the lysed material, such as chromatography and electrophoresis. Electrophoresis can be used to separate different elements (fractions) of a blood sample into individual components, such as proteins to evaluate, diagnose and monitor a variety of diseases and conditions. For example, in a process known as serum protein electrophoresis (SPEP), a lysed blood sample is placed in or on a special medium (e.g., a gel), and an electric current is applied to the gel to cause the protein particles to move through the gel according to the strengths of their electrical charges. These moving proteins form bands or zones that can be detected and identified for use in diagnosing specific diseases.

Cell disruption is generally accomplished by either mechanical or chemical techniques. The type of tissues or cells to be lysed often necessitates certain methods or combinations of methods. Chemical techniques use enzymes or detergents to dissolve the cell walls, and are usually followed by sonication, homogenization, vigorous pipetting or vortexing in a lysis buffer. Mechanical lysing is more widely practiced, and may be accomplished with a mortar and pestle, bead mill, press, blender, grinder, high pressure (e.g., up to 1500 bar), nozzle, or a probe or membrane operated at ultrasonic frequencies. Micromachined devices that use sharp corners or high pressure nozzles to rupture cell walls have also been developed to perform mechanical lysing. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film.

Ultrasonic lysing operates on the basis of generating intense sonic pressure waves in a liquid medium in which the cellular material of interest is suspended. The pressure waves are transferred to the medium with a probe or membrane, and cause the formation of microbubbles that grow and collapse violently, generating shock waves that, if at a sufficiently high energy level, can break cell membranes. One type of known ultrasonic device employs a piezoelectric generator made of lead zirconate titanate crystals to induce vibration in a titanium metal horn or probe tuned to resonate at 15 to 25 kHz. Glass beads may be added to the liquid medium to promote lysis of certain materials.

While lysing techniques and devices of the type describe above have been successfully employed, there is a continuing effort to develop improved devices for performing lysing, as well as to perform pre- and post-lysing steps, such as mixing, agitating or homogenizing a fluid after lysis, or before, during or after other processing performed on lysate, such as incubation and mixing.

SUMMARY OF INVENTION

The present invention provides a method and device for performing lysing on a cell-containing fluid, in which the fluid flows through a vibrating micromachined tube to physically rupture the cell walls (mechanical lysis), and/or to mix, agitate or homogenize the fluid during chemical lysis, and/or to mix, agitate or homogenize the lysate for analysis or other processing after lysing.

According to a first aspect of the invention, the device is a micromachined lysing device comprising the micromachined tube supported by a substrate. The tube includes a fluid inlet, a fluid outlet, and a freestanding portion between the fluid inlet and outlet and spaced apart from a surface of the substrate. The device further includes means for vibrating the freestanding portion of the tube at a level sufficient to rupture the walls of cells in a fluid flowing through the freestanding portion of the tube (mechanical lysing) or to mix the fluid and an appropriate additive (chemical lysing).

In view of the above, the device of this invention is capable of use in various techniques for performing mechanical or chemical lysing by flowing a cell-containing fluid through the micromachined tube, and then vibrating the freestanding portion of the tube as the fluid flows through the tube. According to another aspect of the invention, the micromachined tube is fabricated in or on the surface of the substrate by bulk etching or surface thin-film etching techniques to yield an extremely miniaturized lysing device capable of processing very small quantities of material for analysis. Vibration can be induced in the tube with an electrostatic, piezoelectric or magnetic drive, or another suitable actuation method. By employing mechanical motion induced by a changing electrostatic field, mechanical and electrokinetic forces exist that can promote the rupturing/mixing of the fluid within the tube.

Lysing is often preceded or followed by additional biochemical processing, such as filtration, mixing (homogenization), electrophoresis analysis, chemical reaction, sensing and separation after lysing, as well as fluid diversion, chemical analysis via techniques such as optical transmission or reflection, measurement of dielectric constant, color intensity/chromatography, and injection of the lysed material. In the present invention, such processing can be preformed on the same substrate as the micromachined tube, yielding a one-chip lysing and analysis system.

Other objects and advantages of this invention will be better appreciated from the following detailed description.

DETAILED DESCRIPTION

Figure 1:
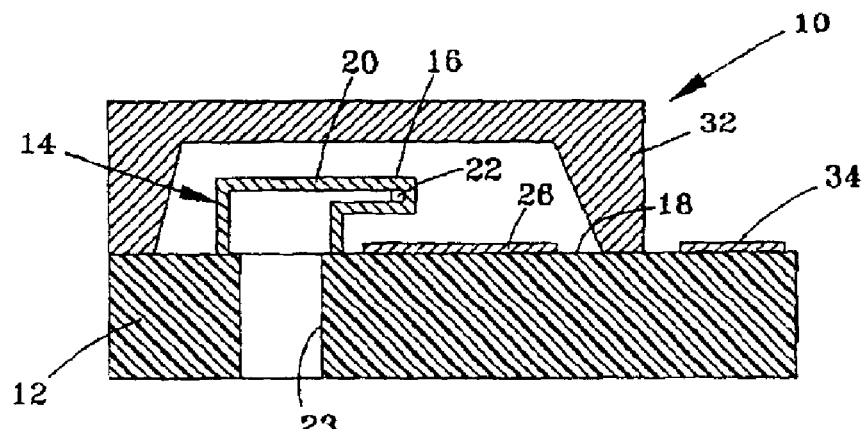
FIGS. 1 and 2 are cross-sectional views of lysing devices with micromachined tubes driven by electrostatic and piezoelectric drives, respectively, in accordance with two embodiments of this invention.
Figure 2:
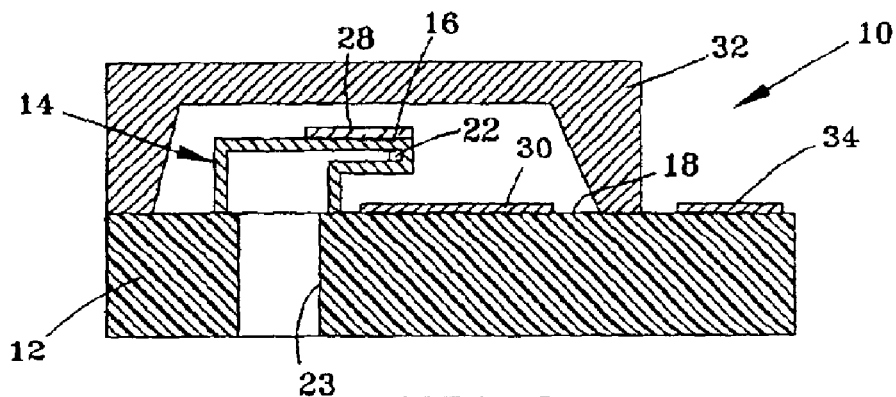

FIGS. 1 and 2 represent lysing devices 10 in accordance with the invention. Each of the devices 10 is shown as being fabricated on a substrate 12, which can be formed of silicon or another semiconductor material, quartz, ceramic, metal or a composite material. A tube 14 is supported by the substrate 12 so as to have a freestanding portion 16 suspended above a surface 18 of the substrate 12. According to the invention, the tube 14 is micromachined from silicon or another semiconductor material, quartz, ceramic, metal or composite material. The tube 14 can either be fabricated entirely from layers of the chosen materials deposited on the substrate 12, or fabricated in part by etching the substrate 12, as will be discussed in more detail below. A fluid inlet 23 is represented as being etched or otherwise formed in the substrate 12 so as to extend through the substrate 12 from a lower surface.

The tube 14 is adapted to serve as a conduit through which a cell-containing fluid flows while the tube 14 is vibrated to either mix the constituents of the fluid or disrupt the walls of the cells (mechanical lysis) in the fluid. Mixing (including agitating and homogenizing) can be used in chemical lysis processes, before electrophoresis to suspend a lysate in a suitable vehicle (e.g., gel), and before, during or after other processing that may follow lysis, such as incubation. Fluids that can be processed with the device 10 include any that contain biological cells or spores from essentially any source, in which the molecular contents of the cells are desired to be released to perform various biological research and development.

The shape and size of the tube 14 are chosen to provide an adequate flow capacity for the fluid and to have vibration parameters that will result in the mixing or lysing effect desired of the device 10. As more readily seen in FIGS. 3 and 4, a suitable configuration for the tube 14 has a pair of legs 20 and an interconnecting cross-member 22, yielding essentially a U-shaped tube 14, though other shapes-both simpler and more complex—are within the scope of this invention. Because micromachining technologies are employed to fabricate the tube 14, the size of the tube 14 can be extremely small, such as lengths of about 0.5 mm and cross-sectional areas of about 100 $\mu m^2$ or more. As a result, the device 10 can be used to process very small quantities of fluid for analysis. In addition to the configuration of the tube 14, other process and structural modifications can be used to improve cell wall fracture. For example, small beads or other particulate matter can be entrained in the fluid to improve cell fracture. A suitable bead size for this purpose is about 1 to about 20 micrometers. The use of beads requires an appropriately sized tube 14, preferably at least 50% larger in cross-section than the beads, e.g., beads having a nominal diameter of up to about 8 micrometers would be suitable for use with a tube 14 having a cross-sectional area of about 100 $\mu m^2$ or more.

The tube 14 is preferably driven at resonance, with the resonant frequency of the tube 14 being controlled by its mechanical design (shape, size, construction and materials). Suitable frequencies are in the range of 1 kHz to over 100 kHz, depending on the particular fluid being lysed. Under most circumstances, frequencies above 10 kHz, including ultrasonic frequencies (those in excess of 20 kHz), will be preferred. The amplitude of vibration is preferably adjusted through the means used to vibrate the tube 14. As shown in FIG. 1, an electrode 26 is located beneath the tube 14 on the surface 18 of the substrate 12. In this embodiment, the tube 14 is formed of doped silicon and can therefore serve as an electrode that can be capacitively coupled to the electrode 26, enabling the electrode 26 to capacitively (electrostatically) drive the tube 14. However, it is foreseeable that the tube 14 could be formed of a nonconductive material, and a separate electrode formed on the tube 14 opposite the electrode 26 for vibrating the tube 14 electrostatically. An alternative driving technique is shown in FIG. 2, in which a piezoelectric element 28 is provided on an upper surface of the tube 14 to generate alternating forces in the plane of the tube 14 that flex the freestanding portion 16 of the tube 14 in directions normal to the plane of the tube 14. Also shown in FIG. 2 is a sensing element 30 for providing feedback to the piezoelectric element 28 to enable the vibration frequency and amplitude to be controlled with appropriate circuitry (not shown) on the substrate 12 or electrically connected through bond pads 34 on the substrate 12. The sensing element 30 can sense the tube 14 capacitively or in any other suitable manner capable of sensing the proximity or motion of the tube 14. While the motion of the tube 14 is represented in FIGS. 1 and 2 as being generated by either electrostatically or piezoelectrically, the tube 14 could be driven magnetically, thermally, or by another actuation technique. An advantage of employing mechanical motion generated by a changing electrostatic field is that agitation of the fluid within the tube 14 can occur as a result of both mechanical and electrokinetic forces on the cells.

FIGS. 1 and 2 show the micromachined tube 14 as being enclosed by a cap 32 bonded or otherwise attached to the substrate 12. In a preferred embodiment, the bond between the cap 32 and the substrate 12 is hermetic, and the enclosure formed by the substrate 12 and cap 32 is evacuated to enable the tube 14 to be driven efficiently at high Q values without damping. A suitable material for the cap 32 is silicon, allowing silicon-to-silicon bonding techniques to be used, though other cap materials and bonding techniques are possible and within the scope of the invention.

Suitable processes for fabricating the tube 14 are disclosed in U.S. patent application Ser. No. 09/468,628 to Srinivas Tadigadapa et al., which is incorporated herein by reference. One particularly suitable method disclosed in Tadigadapa et al. involves etching a trench in a silicon wafer, and then doping the etched surface of the wafer and a surface of a silicon second wafer with boron or another p-type dopant. The doped surfaces of the wafers are then bonded together, such as by fusion bonding, with the result that the trench in the first wafer now defines an enclosed passage between the wafers, with the walls of the passage formed by doped silicon. One of the wafers is then removed by an etchant selective to undoped silicon, and the exposed doped regions are patterned to define the exterior of the tube 14. The surface of the remaining wafer on which the tube 14 is present is then bonded to the substrate 12 so that a portion of the tube 14 is suspended over a cavity etched in the surface of the substrate 12. The remaining wafer is then removed by selective etching so that only the tube 14 remains on the substrate 12. Because the entire tube 14 is formed of doped semiconductor material, a separate electrode is not required on the tube 14 for driving the tube 14 electrostatically with the electrode 26 on the substrate 12.

The above technique is generally a bulk etching process. Surface thin-film techniques can also be used to form the tube 14. An example is to form the tube 14 of layers deposited on a silicon wafer, bonding the wafer to the substrate 12 so that a portion of the tube 14 is suspended over a cavity etched in the surface of the substrate 12, and then removing the wafer by selective etching. These and other potential micromachining techniques are within the scope of this invention.

Figure 3:
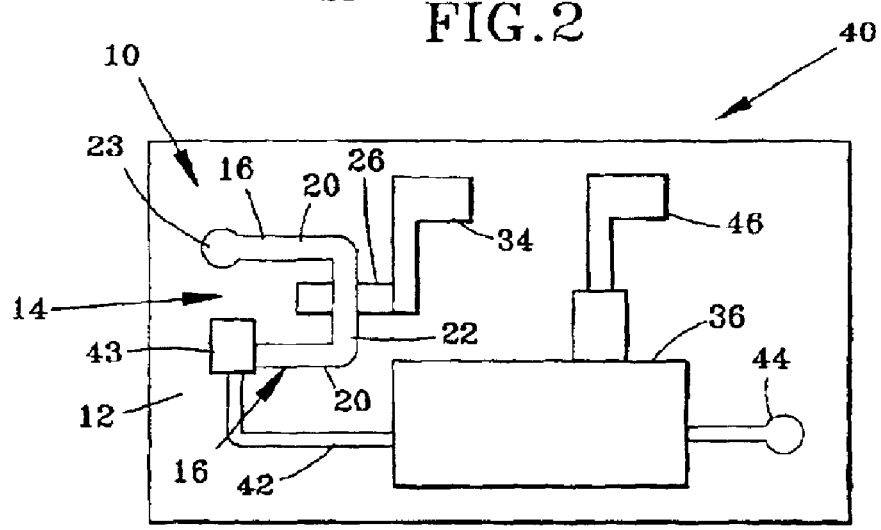
FIGS. 3 and 4 are plan views of mechanical and chemical lysing devices, respectively, each of which includes a micromachined tube and an analysis unit in accordance with the invention.
Figure 4:
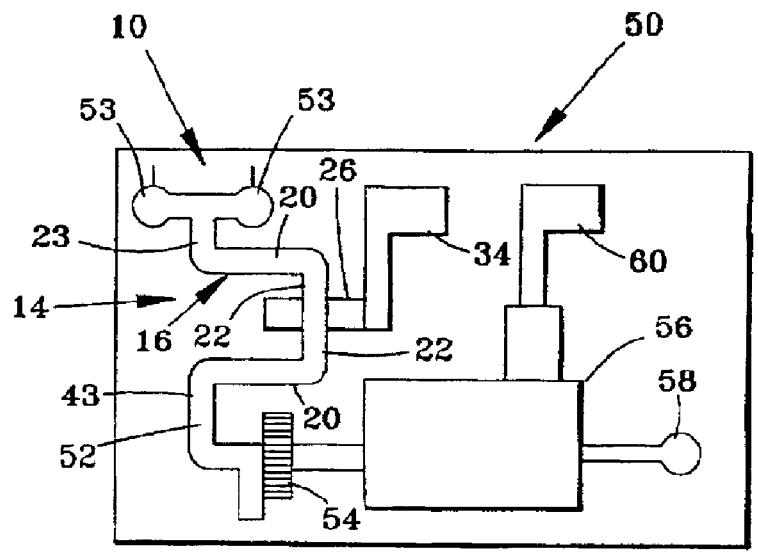

Lysing and chemical mixing are often preceded or followed by additional biochemical processing. A preferred aspect of this invention is the ability to perform additional processing and analysis steps on the same substrate 12 as the tube 14. Examples of such steps include filtration of the lysate, chemical analysis via techniques such as optical transmission or reflection, measurement of the dielectric constant of the lysed material, color intensity/chromatography, mixing or homogenization after lysing, electrophoresis, and injection of the lysed material. FIGS. 3 and 4 schematically represent either of the devices 10 shown in FIG. 1 or 2 integrated with an analysis device on the same substrate 12.

In FIG. 3, the device 10 is represented as part of a mechanical lysis system 40 in which mechanical lysing performed within the tube 14 is followed by chemical reaction and analysis with an appropriate analysis device 36. A fluid outlet 43 of the tube 14 is shown as being connected to the analysis device 36 through a passage 42, which can be adapted to perform any of the above-noted post-lysing processes before the lysed material exits the substrate 12 through an outlet port 44. A bond pad 46 is provided on the substrate 12 through which electrical connection is made with the analysis device 36.

In FIG. 4, the device 10 is represented as being integrated in a chemical lysis system 50, with two separate inlet ports 53 provided upstream of the inlet 23 to the tube 14. The ports 53 allow an additive, such as an enzyme or detergent known in the art, to be introduced into the fluid for performing chemical lysing In this embodiment of the invention, the tube 14 serves to mix or homogenize the lysed material after treatment with the chemical lysing additive, after which the lysed material flows through a passage 52 to an on-chip filtration device 54 and finally a chemical analysis device 56. The filtration device 54 can be fabricated in the surface 18 of the substrate 12 or as a discrete filter element mounted to the substrate 12. Following analysis, the fluid exits the system 50 through a fluid outlet 58 on the substrate 12. A bond pad 60 is provided on the substrate 12 through which electrical connection is made with the analysis device 56.

Figure 5:
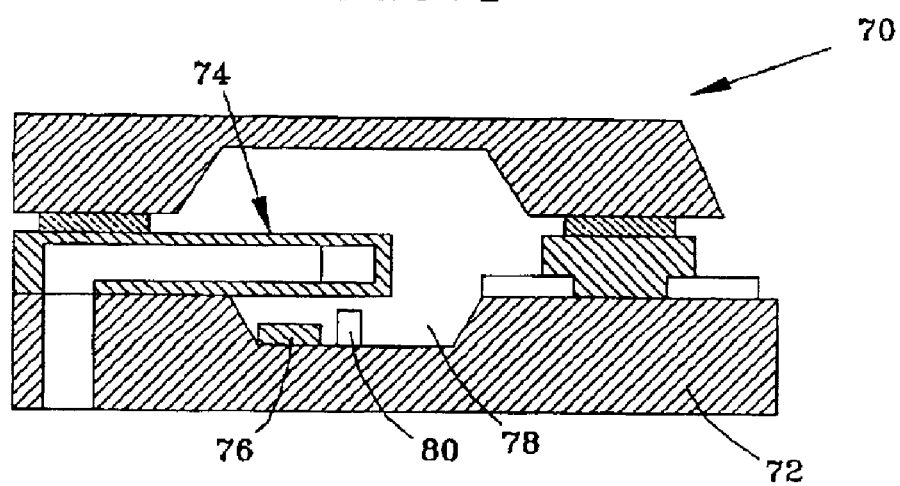
FIG. 5 is a cross-sectional view of a lysing device with a micromachined tube and stop in accordance with another embodiment of this invention.

Depending on the fluid employed and its viscosity, vibration of the tube 14 by itself may not be sufficient to achieve a desired mixing or lysing level. To insure adequate mixing or lysis occurs, the tube 14 can be driven to impact the surface over which it is suspended or a raised feature on the surface, thereby generating greater agitation within the fluid. FIG. 5 represents a mechanical lysing device 70 with a tube 74 micromachined from a layer of semiconductor material deposited on or bonded to a substrate 72, such that the tube 74 is suspended over a cavity 78 defined in the surface of the substrate 72. A raised surface feature 80 can be seen on the surface of the cavity 78 beneath the tube 14 to provide a stop for the tube 74. This feature 80 can be formed by selectively depositing or depositing and then etching a layer of suitable material in the cavity 78 prior to bonding the tube 74 to the substrate 72. When driven at ultrasonic frequencies of sufficient amplitude, the tube 14 can be made to strike the surface feature 80, such that the device 70 operates similarly to an ultrasonic disrupter. The mechanical impact of the tube 74 generates a pressure wave in the fluid as is done in macroscopic sonication systems, leading to mixing or lysing that can be assisted with beads or other particulate material entrained in the fluid. In FIG. 5, the entire tube 74 is represented as being formed of p-type semiconductor material. In such an embodiment, the raised surface feature 80 must be formed of a dielectric material (e.g., an oxide layer) or of a conductive material (e.g., polysilicon) that is electrically tied to the tube 74 so as not to arc when the tube 74 contacts the surface feature 80.

Figure 6:
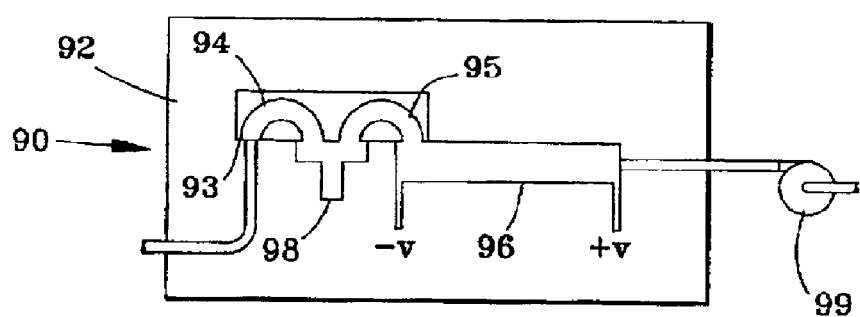
FIG. 6 is a plan view of a one-chip analysis microsystem equipped with micromachined tubes in series for performing lysing and mixing of a cell-containing fluid, and an analysis unit for processing the lysed and mixed fluid in accordance with another embodiment of this invention.

Finally, FIG. 6 represents a one-chip analysis microsystem 90 in which lysis and gel mixing are performed with resonant tubes 94 and 95 suspended in series over a recess 95 and connected to a miniature electrophoresis unit 96 fabricated on the same substrate 92 (chip). The analysis microsystem 90 may be used, for example, to perform DNA separation. The cell-containing fluid to be analyzed enters the first tube 94 in the series through a fluid inlet 93. The tube 94 is caused to vibrate in any suitable manner as discussed previously, and may be used to perform mechanical lysing or to mix the fluid with an additive (e.g., enzyme or detergent) to perform chemical lysing. After leaving the tube 94 and before entering the second tube 95, a suitable gel material of a type known in the art is introduced into the lysate through a port 98. Mixing of the lysate and gel occurs in the tube 95, such that the biological material of the cells is suspended in the gel. The resulting mixture then passes through the electrophoresis unit 96, which may be a transparent microchannel in which electrostatic separation of the biological molecules is performed by electrophoresis in a known manner.

The one-chip microsystem 90 represented in FIG. 6 is schematically shown as being coupled to a fluid pumping device 99. The microsystem 90 can be incorporated with the pumping device 99 to provide a manual handheld or automated system capable of extracting a fluid sample and then lysing and mixing the sample. The pumping device 99 may be a syringe, pipette, electrical or mechanical pump, vacuum line, or any other device capable of introducing or delivering the desired fluid to the microsystem 90. A system of this type is useful in the analysis of small biological samples in the laboratory. Once the vibrating tubes 94 and 95 are filled with the fluid, their resonant frequencies change due to a change in mass. By knowing the fluid density and monitoring the tube frequencies, a user can determine when the tubes 94 and 95 are partially or completely filled with the fluid. With this knowledge, the user can time the lysing and mixing operations that occur within the tubes 94 and 95. Once the lysing and mixing operations are complete, the fluid can be expelled using the same pumping device 99. While represented with the microsystem 90 of FIG. 6, those skilled in the art will appreciate that the pumping device 99 could be incorporated into any of the other devices 10, 40, 50 and 70 represented in FIGS. 1 through 5, such that any of these devices 10, 40, 50 and 70 could be made available as a manual handheld or automated analysis unit. Furthermore, multiple lysing and/or mixing systems formed on the same or separate substrates could be employed in parallel to enable a plurality of samples to be lysed or mixed at the same time.

While the invention has been described in terms of certain embodiments, it is apparent that other forms could be adopted by one skilled in the art. Therefore, the scope of the invention is to be limited only by the following claims.

What is claimed is:

1. A micromachined lysing device comprising:
   a substrate;
   a micromachined tube comprising a fluid inlet, a fluid outlet, and a freestanding portion between the fluid inlet and the fluid outlet, the freestanding portion being spaced apart from a surface of the substrate;
   a cell-containing fluid within the freestanding portion of the tube; and
   means for vibrating the freestanding portion of the tube at a level sufficient to rupture walls of cells in the fluid within the freestanding portion of the tube to produce a lysed material.

2. A micromachined lysing device according to claim 1, wherein the vibrating means comprises:
   a first electrode associated with the freestanding portion of the tube;
   a second electrode associated with the substrate and facing the first electrode; and
   means for applying an electrostatic charge between the first and second electrodes.

3. A micromachined lysing device according to claim 1, wherein the vibrating means comprises a piezoelectric element on a surface of the micromachined tube.

4. A micromachined lysing device according to claim 1, further comprising a cap hermetically bonded to the substrate so as to define a hermetically-sealed enclosure containing at least the freestanding portion of the tube.

5. A micromachined lysing device according to claim 4, wherein the hermetically-sealed enclosure is evacuated.

6. A micromachined lysing device according to claim 1, wherein the substrate has a second surface oppositely disposed from the surface, the tube is disposed at the surface, and at least one of the fluid inlet and the fluid outlet is located at the second surface.

7. A micromachined lysing device according to claim 1, wherein the fluid contains a particulate matter for promoting rupturing of the walls of the cells.

8. A micromachined lysing device according to claim 1, further comprising a raised surface feature on the substrate, the vibrating means being operable to impact the freestanding portion of the tube against the raised surface feature.

9. A micromachined lysing device according to claim 1, wherein the vibrating means is operable to cause the freestanding portion of the tube to resonate.

10. A micromachined lysing device according to claim 1, wherein the tube is a first tube of the micromachined lysing device, the micromachined lysing device further comprising a second tube having a freestanding portion, the second tube being in series with of the first tube.

11. A micromachined lysing device according to claim 10, further comprising means for introducing a gel material into the lysed material after the lysed material leaves the freestanding portion of the first tube and before the lysed material enters the second freestanding portion of the second tube.

12. A micromachined lysing device according to claim 11, further comprising means for vibrating the freestanding portion of the second tube at a level sufficient to mix the lysed material with the gel material.

13. A micromachined lysing device according to claim 12, further comprising means for performing analysis on the lysed material after the lysed material leaves the freestanding portion of the second tube.

14. A micromachined lysing device according to claim 13, wherein the first and second tubes and the analysis means are all supported on the substrate.

15. A micromachined lysing device according to claim 1, wherein the substrate is formed of a semiconductor material and the tube comprises a micromachined portion of the substrate.

16. A micromachined lysing device according to claim 1, wherein the tube comprises a micromachined semiconductor layer on the substrate.

17. A micromachined lysing device according to claim 1, further comprising means on the substrate for filtering cell wall fragments from the lysed material.

18. A micromachined lysing device according to claim 1, further comprising means for delivering the fluid to the tube, the micromachined lysing device and the delivering means defining a handheld analysis unit.

19. A micromachined lysing device comprising:
   a substrate formed of a semiconductor material;
   a micromachined tube formed of a semiconductor material, the tube comprising a fluid inlet, a fluid outlet, and a freestanding portion between the fluid inlet and the fluid outlet, the freestanding portion being spaced apart from a surface of the substrate;
   a cap hermetically bonded to the substrate so as to define a hermetically-sealed enclosure containing at least the freestanding portion of the tube;
   a cell-containing fluid flowing through the tube from the fluid inlet to the fluid outlet;
   means for vibrating the freestanding portion of the tube at a level sufficient to rupture walls of the cells in the fluid as the fluid flows through the freestanding portion of the tube to produce a lysed material that leaves the tube through the fluid outlet;
   means on the substrate for filtering cell wall fragments from the lysed material; and
   means on the substrate for performing analysis on the lysed material after the lysed material is filtered.

20. A micromachined lysing device comprising:
   a substrate;
   a micromachined tube comprising a fluid inlet, a fluid outlet, and a freestanding portion between the fluid inlet and the fluid outlet, the freestanding portion being spaced apart from a surface of the substrate;
   means for introducing a cell-containing fluid and a chemical lysing additive into the tube; and
   means for vibrating the freestanding portion of the tube at a level sufficient to mix the fluid and the chemical lysing additive to produce a lysed material that leaves the tube through the fluid outlet.

21. A micromachined lysing device according to claim 20, wherein the vibrating means comprises:
   a first electrode associated with the freestanding portion of the tube;
   a second electrode associated with the substrate and facing the first electrode; and
   means for applying an electrostatic charge between the first and second electrodes.

22. A micromachined lysing device according to claim 20, wherein the vibrating means comprises a piezoelectric element on a surface of the micromachined tube.

23. A micromachined lysing device according to claim 20, further comprising a cap hermetically bonded to the substrate so as to define a hermetically-sealed enclosure containing at least the freestanding portion of the tube, wherein the hermetically-sealed enclosure is evacuated.

24. A micromachined lysing device according to claim 20, further comprising means for performing analysis on the lysed material.

25. A micromachined lysing device according to claim 24, further comprising means for filtering cell wall fragments from the lysed material.

26. A micromachined lysing device according to claim 25, wherein the tube, the filtering means, and the analysis means are all supported on the substrate.

27. A micromachined lysing device according to claim 20, wherein the substrate is formed of a semiconductor material and the tube comprises a micromachined portion of the substrate.

28. A micromachined lysing device according to claim 20, wherein the tube comprises a micromachined semiconductor layer on the substrate.

29. A micromachined lysing device according to claim 20, further comprising means for delivering the fluid to the tube, the micromachined lysing device and the delivering means defining a handheld analysis unit.

30. A micromachined lysing device comprising:
a substrate formed of a semiconductor material;
a micromachined tube formed of a semiconductor material, the tube comprising a fluid inlet, a fluid outlet, and a freestanding portion between the fluid inlet and the fluid outlet, the freestanding portion being spaced apart from a surface of the substrate;
a cap hermetically bonded to the substrate so as to define a hermetically-sealed enclosure containing at least the freestanding portion of the tube;
a cell-containing fluid and a chemical lysing additive flowing through the tube from the fluid inlet to the fluid outlet;
means for introducing the fluid and the chemical lysing additive into the tube;
means for vibrating the freestanding portion of the tube at a level sufficient to mix the fluid and the chemical lysing additive as the fluid flows through the freestanding portion of the tube to produce a lysed material that leaves the tube through the fluid outlet;
means on the substrate for filtering cell wall fragments from the lysed material; and
means on the substrate for performing analysis on the lysed material after the lysed material is filtered.

31. A method of lysing a cell-containing fluid, the method comprising the steps of:
flowing the fluid through a micromachined tube on a substrate, the tube comprising a fluid inlet, a fluid outlet, and a freestanding portion between the fluid inlet and the fluid outlet, the freestanding portion being spaced apart from a surface of the substrate; and
vibrating the freestanding portion of the tube at a level sufficient to rupture walls of the cells in the fluid as the fluid flows through the freestanding portion of the tube to produce a lysed material that leaves the tube through the fluid outlet.

32. A method according to claim 31, wherein the vibrating step is performed by applying an electrostatic charge between the tube and the substrate.

33. A method according to claim 31, wherein the vibrating step is performed with a piezoelectric element on a surface of the micromachined tube.

34. A method according to claim 31, further comprising the step of introducing a particulate matter into the fluid prior to the fluid entering the freestanding portion of the tube, the particulate matter being introduced in an amount sufficient to promote rupturing of the walls of the cells.

35. A method according to claim 31, wherein the freestanding portion of the tube impacts a portion of the substrate during the vibrating step.

36. A method according to claim 31, wherein the vibrating step causes the freestanding portion of the tube to resonate.

37. A method according to claim 31, further comprising the step of flowing the lysed material through a second tube having a freestanding portion.

38. A method according to claim 37, further comprising the step of introducing a gel material into the lysed material before the lysed material enters the second tube.

39. A method according to claim 38, further comprising the step of vibrating the freestanding portion of the second tube at a level sufficient to mix the lysed material with the gel material.

40. A method according to claim 39, further comprising the step of performing analysis on the lysed material after the lysed material leaves the freestanding portion of the second tube.

41. A method according to claim 40, further comprising the step of filtering cell wall fragments from the lysed material.

42. A method according to claim 41, wherein the filtering step and the analysis step are performed on the substrate.

43. A method of lysing a cell-containing fluid, the method comprising the steps of:
flowing the fluid through a micromachined tube formed of a semiconductor material and supported by a substrate formed of a semiconductor material, the tube comprising a fluid inlet, a fluid outlet, and a freestanding portion between the fluid inlet and the fluid outlet, the freestanding portion being spaced apart from a surface of the substrate and hermetically sealed within an evacuated enclosure defined by a cap bonded to the substrate;
vibrating the freestanding portion of the tube at a level sufficient to rupture walls of the cells in the fluid as the fluid flows through the freestanding portion of the tube to produce a lysed material that leaves the tube through the fluid outlet;
filtering cell wall fragments from the lysed material; and then
performing analysis on the lysed material;
wherein the filtering step and the analysis step are performed on the substrate.

44. A method of lysing a cell-containing fluid, the method comprising the steps of:
flowing the fluid and a chemical lysing additive through a micromachined tube on a substrate, the tube comprising a fluid inlet, a fluid outlet, and a freestanding portion between the fluid inlet and the fluid outlet, the freestanding portion being spaced apart from a surface of the substrate; and
vibrating the freestanding portion of the tube at a level sufficient to mix the fluid and the chemical lysing additive as the fluid and the chemical lysing additive flow through the freestanding portion of the tube to produce a lysed material that leaves the tube through the fluid outlet.

45. A method according to claim 44, the vibrating step is performed by applying an electrostatic charge between the tube and the substrate.

46. A method according to claim 44, wherein the vibrating step is performed with a piezoelectric element on a surface of the micromachined tube.

47. A method according to claim 44, wherein the vibrating step is performed within a hermetically-sealed enclosure containing at least the freestanding portion of the tube.

48. A method according to claim 47, wherein the hermetically-sealed cavity is evacuated.

49. A method according to claim 44, further comprising the step of performing analysis on the lysed material.

50. A method according to claim 49, further comprising the step of filtering cell wall fragments from the lysed material before performing the analysis.

51. A method according to claim 50, wherein the filtering step and the analysis step are performed on the substrate.

52. A method of lysing a cell-containing fluid, the method comprising the steps of:

flowing the fluid and a chemical lysing additive through a micromachined tube formed of a semiconductor material and supported by a substrate formed of a semiconductor material, the tube comprising a fluid inlet, a fluid outlet, and a freestanding portion between the fluid inlet and the fluid outlet, the freestanding portion being spaced apart from a surface of the substrate and hermetically sealed within an evacuated enclosure defined by a cap bonded to the substrate;

vibrating the freestanding portion of the tube at a level sufficient to mix the fluid and the chemical lysing additive as the fluid and the chemical lysing additive flow through the freestanding portion of the tube to produce a lysed material that leaves the tube through the fluid outlet, filtering cell wall fragments from the lysed material; and then performing analysis on the lysed material;

wherein the filtering step and the analysis step are performed on the substrate.

* * * * *